US00PP28748P3

(12) United States Plant Patent
Danziger

(10) Patent No.: US PP28,748 P3
(45) Date of Patent: Dec. 5, 2017

(54) ***CALIBRACHOA* PLANT NAMED 'DANOAPRINC'**

(50) Latin Name: *Calibrachoa hybrida*
Varietal Denomination: DANOAPRINC

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 14/999,066

(22) Filed: Mar. 25, 2016

(65) Prior Publication Data

US 2017/0280611 P1 Sep. 28, 2017

(51) Int. Cl.
*A01H 5/02* (2006.01)

(52) U.S. Cl.
USPC ..... Plt./413

(58) Field of Classification Search
USPC ..... Plt./413
CPC ..... A01H 5/02
See application file for complete search history.

(56) References Cited

PUBLICATIONS http://nova.co.at/marsNova/en/instance/picture/Calibrachoa-Noa--Princess.xhtml?oid=9526828; Feb. 17, 2016; 3 pages.*

* cited by examiner

*Primary Examiner* — Kent L Bell
(74) *Attorney, Agent, or Firm* — Cassandra Bright

(57) ABSTRACT

A new and distinct *Calibrachoa* cultivar named 'DANOAPRINC' is disclosed, characterized by a semi-trailing compact habit and moderate branching. Flowers are large and uniquely light pink with purple veins and darker pink stripes along the petals with a yellow center. The new variety is a *Calibrachoa*, normally produced as an outdoor garden or container plant.

2 Drawing Sheets

Figure 1:
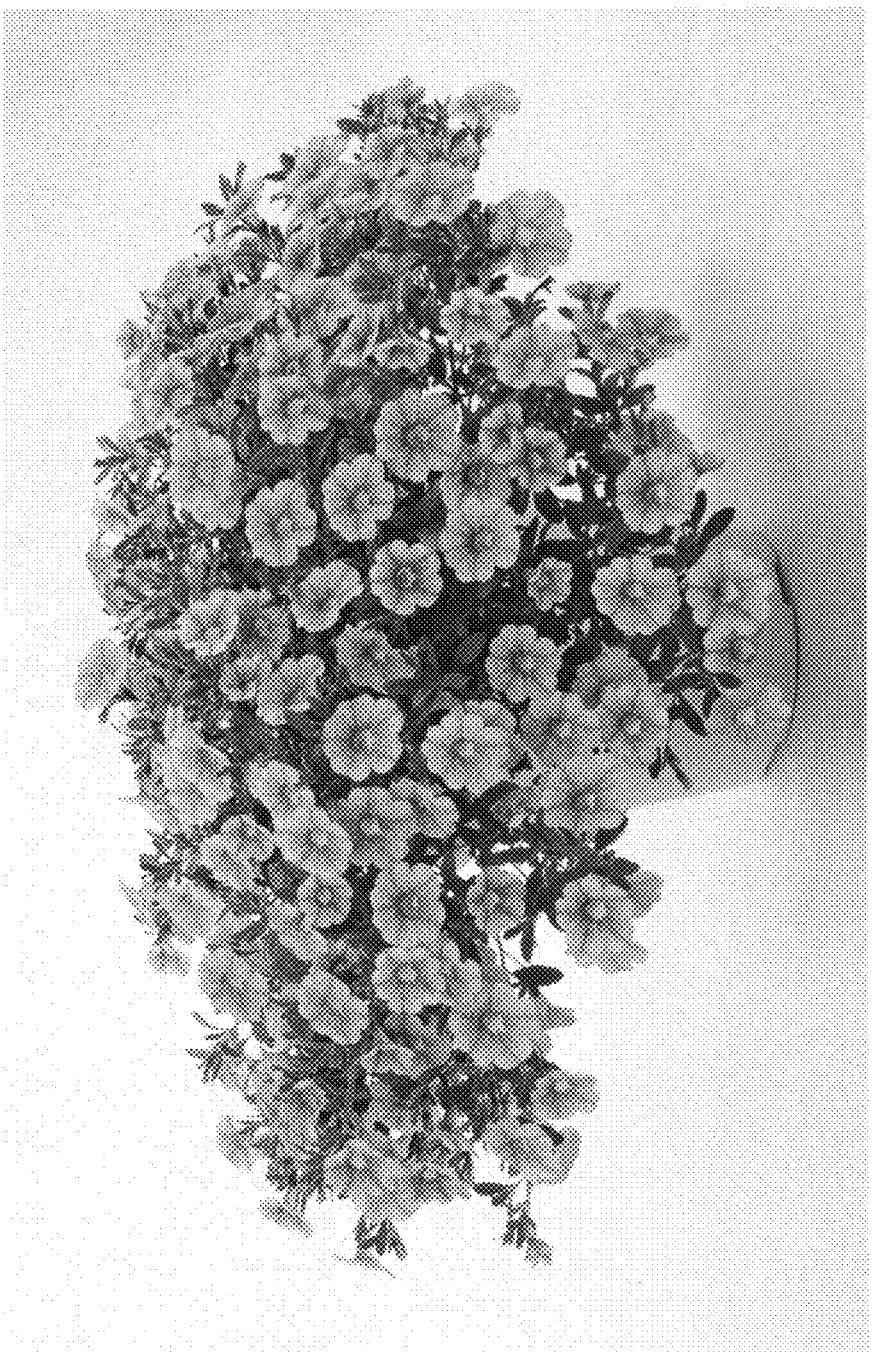

Latin name of the genus and species: *Calibrachoa hybrida.*

Variety denomination: 'DANOAPRINC'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties. The open pollination resulting in this new variety was made during January of 2012.

The seed parent is the unpatented, propriety variety referred to as *Calibrachoa* 'cv. 11-2622'. The pollen parent is unknown as it was an open pollination breeding program. The new variety was discovered in August of 2012 by the inventor in a group of seedlings resulting from the 2012 crossing, in a greenhouse in Moshav Mishmar Hashiva, Israel.

Asexual reproduction of the new cultivar 'DANOAPRINC' was first performed by terminal vegetative cuttings during September of 2012, at a greenhouse in Moshav Mishmar Hashiva, Israel. Subsequent propagation by vegetative cuttings has shown that the unique features of this cultivar are stable and reproduced true to type in more than 20 successive generations.

SUMMARY OF THE INVENTION

The cultivar 'DANOAPRINC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOAPRINC' These characteristics in combination distinguish 'DANOAPRINC' as a new and distinct *Calibrachoa* cultivar:

1. Semi-trailing growth habit.
2. Moderately branched growth habit.
3. Flower color is a unique combination of light pink with purple veins, darker pink stripes along the inner petal surface at the point of fusion and a yellow center.
4. Large flower size.
5. Compact plant.

PARENT COMPARISON

Plants of the new cultivar 'DANOAPRINC' are similar to plants of the seed parent, *Calibrachoa* 'cv. 11-2622' most horticultural characteristics, however, plants of the new cultivar 'DANOAPRINC' differ in the following;

1. Semi-trailing growth habit, whereas the seed parent has a trailing growth habit.
2. Less well branched than the seed parent.
3. Flower color is light pink with purple vein, darker stripes along the petals and a yellow center, whereas the seed parent has white flowers.
4. Larger flowers than the seed parent.
5. Compact growth form, whereas the seed parent has a medium size growth form.

COMMERCIAL COMPARISON

Plants of the new cultivar 'DANOAPRINC' can be compared to the patented commercial variety *Calibrachoa*

'DANOA49' U.S. Plant Pat. No. 22,050. These varieties are similar in most horticultural characteristics; however, 'DANOAPRINC' differs in the following:

1. The comparator is a medium sized plant, while the new variety is a compact plant.
2. The comparator is very well branched, while the new variety is moderately branched.
3. Flower color of comparator is dark pink with a white center, while flower color of the new variety is light pink with purple veins, darker pink stripes along the petals and a yellow center.
4. Flowering time of the comparator is earlier than that of the new variety.
5. The comparator has more flowers per plant than the new variety.

Plants of the new cultivar 'DANOAPRINC' can also be compared to the patented commercial variety *Calibrachoa* 'DANOA53' U.S. Plant Pat. No. 22,056. These varieties are similar in most horticultural characteristics; however, 'DANOAPRINC' differs in the following:

1. The comparator is a medium-vigorous sized plant, while the new variety is a compact plant.
2. The comparator is very well branched, while the new variety is moderately branched.
3. Flower color of comparator is light pink with a dark pink center, while flower color of the new variety is light pink with purple veins, with darker pink stripes along the petals and a yellow center.
4. Flowering time of the comparator is earlier than that of the new variety.
5. The comparator has more flowers than the new variety.

BRIEF DESCRIPTION OF THE PHOTOGRAPHS

The accompanying photograph in FIG. 1 illustrates in full color a typical plant of 'DANOAPRINC' grown in containers overwintered in an unheated hoop house, in Moshav Mishmar Hashiva, Israel.

Figure 2:
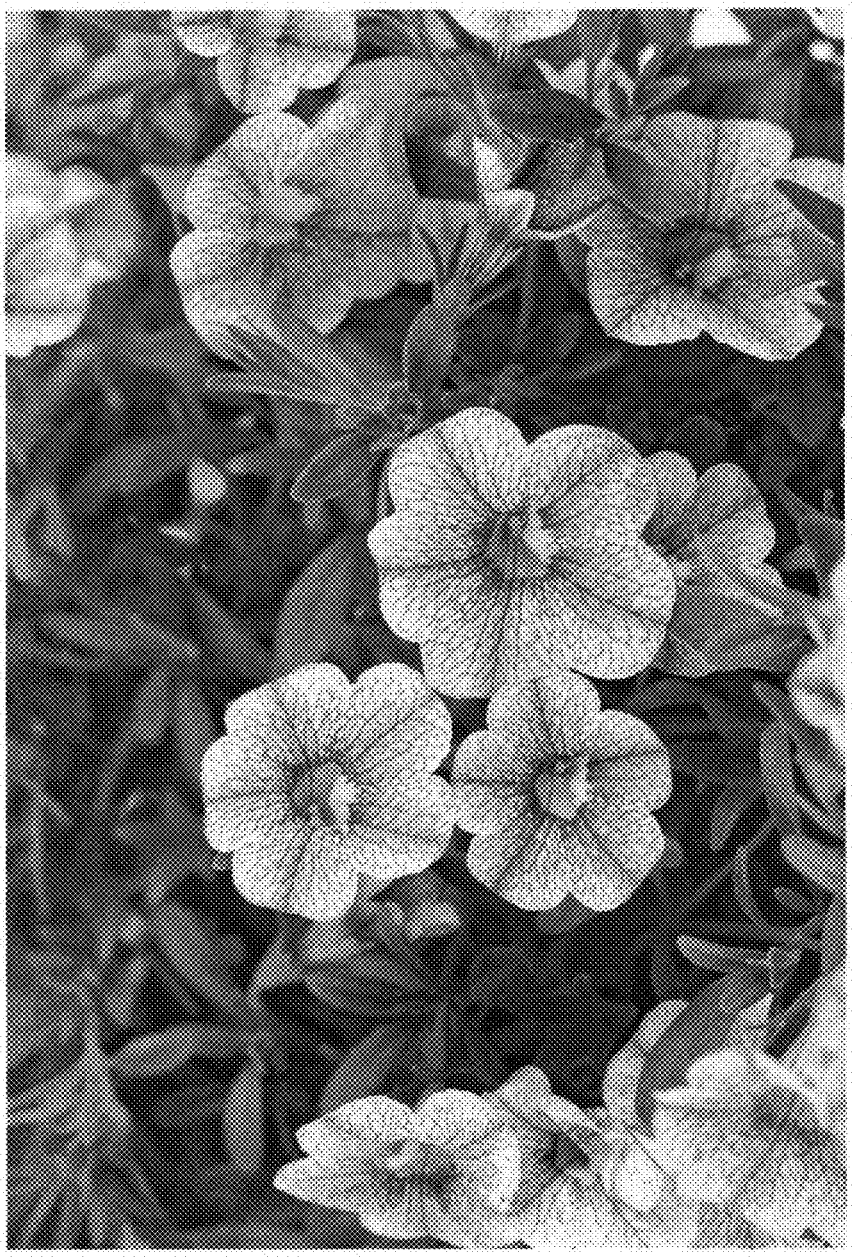

FIG. 2 illustrates in full color a typical inflorescence of 'DANOAPRINC'. Age of the plant photographed is approximately 60 days from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DANOAPRINC' plants grown in a greenhouse in Moshav Mishmar Hashiva, Israel, under natural lighting. Measurements were taken during April of 2015. The plants were approximately 60 days from a rooted cutting in a 13 cm pot. The growing temperature ranged from 18° C. to 35° C. during the days, 15° C. to 25° C. during the nights. Measurements and numerical values represent averages of typical plant types.

Botanical classification: *Calibrachoa hybrida* 'DANOAPRINC'.

PROPAGATION

Time to initiate roots: 10-14 days at approximately 20-22° C.

PLANT

Growth habit: Semi trailing.
Pot size of plant described: 13 cm.
Height: About 8 cm to top of flowering plane.
Plant spread: About 40 cm.
Growth rate: Medium to low vigor, forming a compact plant.
Branching characteristics: Moderately branched.
Length of primary lateral branches: About 20 cm.
Diameter of lateral branches: About 0.2 cm.
Quantity of primary lateral branches: 8.
Characteristics of primary lateral branches:
*Form*.—Cylindrical.
*Diameter*.—About 0.2 cm.
*Color*.—RHS Yellow-Green N144 B.
*Texture*.—Slightly pubescent.
*Strength*.—Strong.
Internode length: About 1 cm.
Root description: Fibrous.

FOLIAGE

Leaf:
*Arrangement*.—Alternate.
*Quantity*.—Approximately 50 per branch.
*Average length*.—3.5 cm.
*Average width*.—1.2 cm.
*Shape of blade*.—Elliptic.
*Apex*.—Rounded.
*Base*.—Acute.
*Margin*.—Entire.
*Texture of top surface*.—Velvety.
*Texture of bottom surface*.—Velvety.
*Pubescence*.—Pubescent.
*Color*.—Young foliage upper side: RHS Yellow-Green 146 A. Young foliage under side: RHS Yellow-Green 146 B. Mature foliage upper side: RHS Yellow-Green 147 A. Mature foliage under side: RHS Yellow-Green 147 B.
*Venation*.—Type: Pinnate. Venation color upper side: RHS Yellow-Green 147 A. Venation color under side: RHS Yellow-Green 147 C.
*Petiole*.—Length: about 0.5 cm. Diameter: about 0.2 cm. Color: RHS Yellow-Green 147 A. Texture: Velvety.

FLOWER

Natural flowering season: Spring, Summer and Autumn under natural conditions in Israel.
Days to flowering from rooted cutting: About 40 days.
Inflorescence and flower type and habit: Axillary, single flower, salverform shape, Upright and outwardly facing.
Rate of flower opening: 3 to 4 days from bud to fully opened flower.
Flower longevity on plant: 4-7 days.
Approximate quantity of flowers per plant: About 50.
Persistent or self-cleaning: Self-cleaning.
Bud:
*Shape*.—Tubular.
*Length*.—About 3.0 cm.
*Diameter*.—About 0.9 cm.
*Color*.—RHS Red-Purple 62 D with Purple veins RHS Red-Purple 64 A.
Flower size:
*Diameter*.—About 4.0 cm.
*Length*.—About 2.5 cm.
*Flower tube diameter at distal end*.—About 1.0 cm.
*Flower tube diameter at proximal end*.—About 0.4 cm.

Petals:

*Length from throat*.—About 1.5 cm.

*Width*.—About 2 cm.

*Quantity*.—5.

*Texture*.—Velvety.

*Apex*.—Rounded.

*Base*.—Fused.

*Margin*.—Entire.

Color:

*When opening*.—Upper surface: RHS Red-Purple 63 C with Purple veins and stripes along the petals RHS Red-Purple N 74 A and a Yellow center RHS Yellow 2 A. Lower surface: RHS Red-Purple 62 D with Purple veins RHS Red-Purple 64 A.

*Fully opened*.—Upper surface: RHS Red-Purple 63 D with Purple veins and stripes along the petals RHS Red-Purple N 74 A and a Yellow center RHS Yellow 2 A. Lower surface: RHS Red-Purple 62 D with Purple veins RHS Red-Purple 64 A.

*Flower throat* (*inside*).—RHS Yellow 2 A.

*Flower throat, vein*.—RHS Red-Purple 64 A.

*Flower tube* (*outside*).—RHS Yellow 5 B.

*Flower tube, vein*.—RHS Red-Purple 64 A.

*Petal color, fading to*.—RHS Red-Purple 63 D with Purple veins and stripes along the petals RHS Red-Purple N 74 B and a Yellow center RHS Yellow 2 B.

Calyx/sepals:

*Quantity per flower*.—5.

*Shape*.—Elliptic.

*Length*.—About 1.5 cm.

*Width*.—About 0.5 cm.

*Apex*.—Acute.

*Base*.—Fused.

*Margin*.—Entire.

*Texture*.—Velvety.

*Color*.—Upper Surface: RHS Yellow-Green 147 A.

*Lower surface*.—RHS Yellow-Green 147 B.

Peduncle: Not relevant.

Pedicel:

*Length*.—About 2 cm.

*Diameter*.—About 0.1 cm.

*Color*.—RHS Yellow-Green N144 A.

*Orientation*.—45 degrees from attachment.

Fragrance: None.

REPRODUCTIVE ORGANS

Stamens:

*Number*.—5.

*Filament length*.—About 1 cm.

Anthers:

*Length*.—About 0.1 cm.

*Shape*.—Rounded.

*Color*.—RHS Yellow 7 D.

*Pollen*.—Color: RHS Yellow 7 B. Quantity: moderate amount.

Pistil:

*Number*.—1.

*Length*.—About 1.2 cm.

*Style*.—Length: about 1.0 cm. Color: RHS Yellow-Green 1 C.

*Stigma*.—Shape: Rounded. Color: RHS Yellow-Green N144 C. Ovary Color: RHS Yellow-Green N 144 D.

OTHER CHARACTERISTICS

Seeds and fruits: About 30 brown, rounded seeds of about 0.5 mm diameter, per one brown, conical capsule.

Disease/pest resistance: Typical to known *Calibrachoa* varieties. Neither resistance nor susceptibility to the normal diseases and pests of *Calibrachoa* have been observed. Pests common to *Calibrachoa* include Aphids and thrips. Typical diseases are *Botrytis* and *Pythium*.

Temperature tolerance: 5° C. to 30° C.

Drought tolerance: No tolerance for drought.

What is claimed is:

1. A new and distinct cultivar of *Calibrachoa* plant named 'DANOAPRINC' as herein illustrated and described.

* * * * *